United States Patent [19]

Laing

[11] Patent Number: 5,399,166
[45] Date of Patent: Mar. 21, 1995

[54] PORTABLE INFUSION DEVICE

[76] Inventor: David H. Laing, 16A Henry Street, Toronto, Ontario, Canada, M5T 1X1

[21] Appl. No.: 155,220

[22] Filed: Nov. 22, 1993

[30] Foreign Application Priority Data

Nov. 23, 1992 [CA] Canada .................. 2083555

[51] Int. Cl.$^6$ .................. A61M 1/00; A61M 37/00
[52] U.S. Cl. .................. 604/146; 604/131; 604/141
[58] Field of Search ............. 604/131, 141, 146, 147; 222/95, 100

[56] References Cited

U.S. PATENT DOCUMENTS

| | | | |
|---|---|---|---|
| 3,756,459 | 9/1973 | Bannister et al. | 604/146 |
| 3,895,741 | 7/1975 | Nugent | 604/141 |
| 4,077,405 | 3/1978 | Haerten et al. | 128/214 |
| 4,237,881 | 12/1980 | Beigler et al. | 604/141 |
| 4,267,834 | 5/1981 | Barger et al. | 128/214 |
| 4,430,078 | 2/1984 | Sprague | 604/141 |
| 4,443,218 | 4/1984 | DeCant, Jr. | 604/67 |
| 4,504,267 | 3/1985 | Parmelee et al. | 604/134 |
| 4,557,726 | 12/1985 | Reinicke | 604/67 |
| 4,613,327 | 9/1986 | Tegrarian et al. | 604/141 |
| 4,670,006 | 6/1987 | Sinnett et al. | 604/26 |
| 4,684,367 | 8/1987 | Schaffer et al. | 604/141 |
| 4,735,613 | 4/1988 | Bellin et al. | 604/141 |
| 4,998,914 | 3/1991 | Wiest et al. | 604/67 |
| 5,059,182 | 10/1991 | Laing | 604/142 |
| 5,163,909 | 11/1992 | Stewart | 604/131 |
| 5,207,645 | 5/1993 | Ross et al. | 604/141 |
| 5,290,240 | 3/1994 | Horres, Jr. | 604/141 |

FOREIGN PATENT DOCUMENTS

| | | | |
|---|---|---|---|
| 61546/86 | 5/1987 | Australia. | |
| 1152823 | 8/1983 | Canada | 119/78 |
| 2021284 | 1/1991 | Canada. | |
| 0277518 | 8/1988 | European Pat. Off. . | |
| WO87/05225 | 9/1987 | WIPO . | |
| WO90/07942 | 7/1990 | WIPO . | |

Primary Examiner—John G. Weiss

[57] ABSTRACT

An infusion device including a rigid accessible housing, a flexible air bag contained within the rigid housing in use, a space next to the flexible air bag for containing a drug bag in use, a line connected between the drug bag and patient in use, a pumping device connected to the air bag, a control unit for controlling the operation of the pump which includes a sensing mechanism in communication with the line or drug bag for sensing the fluid pressure therein without contaminating the medicament in the line to the patient and wherein the pumping device is activated when the pressure in the line or drug bag passes below a predetermined level.

9 Claims, 8 Drawing Sheets

PORTABLE INFUSION DEVICE

FIELD OF INVENTION

This invention relates to infusion devices for precise administering of medicaments to patients and finds particular application in portable infusion devices.

BACKGROUND OF THE INVENTION

It is known in the art to which the present invention pertains, to provide devices which deliver a fluid medicament from a drug bag to a line leading to an infusing needle or catheter. Many such devices utilize mechanical pumping means for delivering the fluid i.e. peristaltic pumps, etc. As well, it is known in the art to provide means for controlling the rate at which the fluid is delivered.

For example, Australian Patent Application No. 61546/86 to Cannon et al. published May 28, 1987 teaches an infusion device which includes a peristaltic pump that is used in association with a strain gauge assembly which monitors dimensional changes in the outer diameter of an I.V. tube. The fluid flow through the infusion tube is motivated by the pump which, through a series of fingers which massage the I.V. tube, cause the fluid flow. The rate of fluid delivery is determined from a reading from the strain gauge. From this determination, a controller operates the pump to vary the rate of flow, if necessary. There are disadvantages to the use of mechanical means such as peristaltic pumps to deliver fluids, including the costs associated with such fluid pumps which include the costs of maintaining the pump. Further, the fluid to be delivered is gravity fed from a reservoir thereby interfering with the portability of the system.

Other references which include direct displacement pumping means include U.S. Pat. Nos. 4,670,006 to Sinnett et al. and 4,998,914 to Wiest et al.

U.S. Pat. No. 4,670,006 teaches an infusion device which includes an electrically driven fluid pump combined with a pressure regulator and pressure detecting means, as well as a motor control unit for the pump. The device monitors the fluid delivery pressure and activates the fluid pump when the pressure falls below a predetermined level. As already stated above, the use of a pump assembly for pumping a fluid directly provides certain disadvantages in both costs and maintenance. Further, the configuration of detection and control means is not practical for use in a portable infusion unit.

U.S. Pat. No. 4,998,914 describes a perfusion system which uses a perfusion pump connected with a perfusion line having a pressure sensor for determining the flow rate of fluid to be delivered. This device also provides for gravity feeding of the perfusion fluid to the pump. The perfusion system monitors the pressure within the body cavity being perfused. This is useful in such a perfusion system, but not necessary for use in an infusion system. Again, the cost and maintenance of the fluid pump poses certain disadvantages, as does the gravity feed of the pump.

PCT application WO 90/07942 to Wojcicki et al. purports to teach a fluid delivery system which includes a volumetric pump and a method of continuously monitoring the operation of the delivery system for controlling the pump. The control method of this reference is characterised by the measurement of actual pressure of delivery of a fluid with every cycle of the volumetric pump. Such measurement requires certain electronic sensing and calculation means which add to the cost and complexity of the infusion system. Again, as stated above, volumetric pumps have disadvantages relating to both cost and maintenance.

European patent application 277,518 to Heitmeier et al. discloses a pressure infusion device, again in which an infusion pump is used to control the rate of flow of the infused liquid. The infusion pump is operated by a control circuit which measures the rate of flow of infused liquid between two sensors which are separated along the infusion tube. The volume of flow is calculated and the controller adjusts the speed of the pump, if necessary. Gravity feed is used to supply the pump thereby reducing the portability of the system. Again, the use of an infusion pump will add to the cost and maintenance disadvantages of the system, as will the electronics required to control the infusion pump on the basis of measurements made between the two sensors. The gravity feed will limit the portability of the system.

It is also known in the art to which the present invention pertains, to provide infusion devices which transfer a fluid medicament from a drug bag or reservoir using means to pressurize the drug bag or reservoir. The pressurizing means is useful in combination with a flow regulator which is part of the delivery line.

U.S. Pat. No. 4,267,834 to Barger et al. discloses a device for flushing a medical fluid through an infusion line used for monitoring blood pressure fluctuations. The rate at which the fluid is infused to the patient is controlled in part through a compression sleeve connected to a pressure gauge and adjustable using a squeeze bulb. Although simple to operate, the flowrate of fluid through the infusion tube is not precisely controlled as the pressure to the drug bag must be monitored and adjusted manually. Such an infusion system would not be practical for the infusing of a drug at a constant flow rate.

U.S. Pat. No. 5,059,182 to the present inventor, describes a portable infusion device which includes an inflatable bag carried in a container within which a drug bag filled with a fluid to be infused is placed. The pressure imparted by the inflatable bag to the drug bag motivates the fluid therein to flow through a tube to the patient to which the fluid is being delivered. Flow rate control is achieved through the use of a flow regulator in combination with the monitoring the pressure imparted by the inflatable bag on the drug bag. Again, the flow rate control of infused fluid is not easily maintained as constant monitoring and manual adjustment of the pressure of the inflatable bag is necessary.

U.S. Pat. No. 4,505,264 to Parmelee et al. describes a portable infusion device in which a drug bag containing a fluid to be infused is placed within a rigid container having a spring biased plate to impart a pressure on the drug bag to motivate the fluid to flow into the connecting tube. The flow rate is controlled by regulators connected in series with the tube. The use of the spring biased plate results in a variable pressure imparted to the drug bag as the drug bag drains (i.e. over the range of movement of the spring biased plate). As a result, higher flow rates will be experienced initially, compared to lower flow rates which will be experienced when the drug bag nears depletion. This variable flow rate is unacceptable in a fluid infusing device.

U.S. Pat. No. 4,557,726 to Reinicke describes a medication dispensing system in which a medication to be infused fills a reservoir over which a constant pressure is maintained through the use of a fluid which has two-phases (gas and liquid) body temperature. The flow through the infusion tube is controlled by means of a regulator. The pressure of the fluid infusate is not utilized or adjusted to maintain a constant flow rate of infusate to the patient.

Similarly, Canadian Patent No. 1,152,823 to Dorman and Canadian Patent No. 2,021,284 to Sampson both also utilize regulator devices in series with an infusate line maintained at a constant pressure for controlling the flow infusate to the patient. Neither reference discloses a manner of measuring and thereby controlling the pressure of infusate to regulate the flow to the patient.

U.S. Pat. No. 4,077,405 to Haerten et al. discloses an apparatus for infusing liquids wherein a supply reservoir of the infusate liquid is maintained at a pressure in excess of the pressure prevailing at the point of liquid discharge to the patient. Preselectable constant volumes of liquid are discharged at periodic intervals in accordance with a treatment program. Again the control of the flow rate of infusate is not controlled by measuring the pressure of the infusate.

U.S. Pat. No. 4,443,218 to DeCant, Jr. et al. discloses a infusion apparatus in which the flow of infusate is controlled by the measurement of a differential pressure across a flow path through which a higher viscosity fluid is forced to flow as a result of the flow of the infusate. By responding to a measurement of the pressure drop across a flow restriction, an electric motor may be used transmit mechanical pressure to the infusate chamber to adjust the infusate flow rate. Again, the control of the flow of infusate is not related to a direct measurement of the pressure of the infusate.

PCT application WO 87/05225 to Kamen discloses a fluid dispensing system in which a infusate is transferred into a dispensing means contained in an isolated region, the amount of infusate transferred into the dispensing means determined by measuring the amount of a gas displaced from the isolated region surrounding the dispensing means. The infusate is then transferred from the dispensing means and another measurement of the gas reentering the isolated region is made. By comparing the amounts of displaced and replaced gas, it is possible to determine the amount of infusate which has been dispensed. Again, no measurement of the infusate pressure is made to determine the flow rate of infusate.

Nowhere in the prior art references is there an infusion device which overcomes many of the disadvantages of the prior art and thereby provides an infusion device which is preferably portable and includes an infusate pressure monitoring control loop adjusting infusate flow.

As well, the prior art does not disclose a means for responding to changes in infusate pressure to control the desired infusate flow rate, which is both inexpensive and in which the infusate is not contaminated.

It is therefore a primary object of the present invention to provide an infusion device which is portable and allows the administration of fluid medicaments to patients without the patient needing to be restricted to a hospital or clinic.

It is a further object of the present invention to provide an infusion device which is safe and reliable to use.

It is yet a further object of the present invention to provide an infusion device which monitors or responds to the infusate pressure and includes means to maintain the infusate pressure at a desired level.

It is another object of the present invention to provide an infusion device which is inexpensive.

Further and other objects of this invention will become apparent to those skilled in the art when considering the following summary of invention and the more detailed description of the preferred embodiments illustrated herein.

SUMMARY OF THE INVENTION

According to an aspect of the present invention there is provided an infusion device for fluids comprising a rigid frame or housing, the frame or housing having disposed therewith when assembled a space wherein is disposed in use a flexible bag previously evacuated of air and filled with a fluid, the flexible bag having an outlet and having a first tube having two ends connected thereto in use for carrying the fluid from the flexible bag proximate one end of the first tube to the distal end of the first tube proximate the patient in use; the housing containing in use means to press the fluid bag and cause flow of fluid through the first line to the patient; the infusion device having means to change (such as increase/decrease) the ability of the means to press the fluid bag, to press the fluid bag, the infusion device having sensing means to sense the pressure of the fluid in the first line; the infusion device having control means having set points therewith in use for desired fluid pressure in the first line and in communication with the means to press the fluid bag and to receive sensed fluid pressure from the sensing means and to respond to high/low pressures sensed by activating the means to increase/decrease the ability of the means to press the fluid bag to press the fluid bag, a second line having two ends and connected with the first line proximate one end of the second line intermediate the ends of the first line, and having disposed proximate the other end of the second line isolation means to present a pressure in the fluid to the sensing means without the sensing means contaminating the fluid being delivered to the patient in use, wherein in use as the fluid bag is pressed fluid passes to the patient through the first line depleting the volume of fluid in the fluid bag, which fluid communicates a pressure in the second line to the isolated sensing means without contaminating the fluid being delivered to the patient, the control means responding to changes in the fluid pressure by activating/deactivating the means to change (such as increase/decrease) the ability of the means to press the fluid bag to press the fluid bag.

Preferably, the infusion device is contained within a shoulder bag or the like to increase the mobility of the patient. The means to press the fluid bag or the air bag, and the fluid bag may be separated within the frame or housing of the infusion device by a hinged moveable plate which assists in ensuring equal pressure is being exerted over the length of the fluid bag.

A flow restrictor may be placed before the needle of the second line for precise administration of the drug.

The isolation member may include a sock or diaphragm made from extremely thin flexible impermeable material contained in a chamber attached at one end to the third line and to the sensing means at the other end thereof, the chamber presenting a liquid filled section within the sock or on one side of the diaphragm and an air filled space on the other side of the sock or diaphragm, wherein the flexible sock or diaphragm is contained in the chamber so that in use the fluid acts to produce a pressure reading to the sensing means via the air space on the air side of the sock or diaphragm.

According to another aspect of the present invention there is provided a portable infusion device comprising: (a) a rigid housing, the housing having an interior space; (b) a flexible bag contained within the interior space, the flexible bag filled with a fluid to be delivered, the flexible bag having an outlet; (c) a tube having a first end attached to the flexible bag outlet in flow communication with the fluid to be delivered, the tube having a second end to which the fluid is delivered in use; (d) an inflatable bag contained within the interior space, the inflatable bag inflatable to press the flexible bag thus creating a fluid pressure within the flexible bag causing a tendency for the fluid to flow from the flexible bag through the tube for delivery to the second end of the tube; (e) means for inflating the inflatable bag in response to a signal; (f) control means which responds to the fluid pressure within the flexible bag for generating the signal when the fluid pressure in the flexible bag is less than a desired fluid pressure, said control means comprising: (i) a substantially inflexible base member; (ii) a resilient spring plate having a first end and a second end, said plate attached to said base member at said first end, said second end free to flex toward and away from said base member, said second end biased toward said base member; (iii) a bladder in flow communication with said flexible bag wherein said bladder inflates in response to an increase in said fluid pressure and deflates in response to a decrease in said fluid pressure, said bladder compressed by said plate between said second end of said plate and said base member such that said second end of said plate flexes away from said base member in response to an inflation of said bladder and flexes toward said base member in response to a deflation of said bladder; and (iv) means to generate said signal when said plate flexes toward said base member in response to a deflation of said bladder in response to a decrease in said fluid pressure to less than said desired fluid pressure.

Preferably, (a) the resilient spring plate comprises a thin metal plate; (b) the inflating means comprises an electric air pump and an air pump power supply, the air pump inflating the inflatable bag in reponse to an electrical current from the air pump power supply; and (c) the signal generating means comprises a normally open switch circuit electrically connected in series between the electric air pump and the air pump power supply, the switch circuit closed by the second end of the metal plate when flexed toward the base member in response to a deflation of the bladder in response to a decrease in the fluid pressure to less than the desired fluid pressure.

According to yet another aspect of the present invention, there is provided for in a portable infusion device, means for controlling delivery of a fluid from a flexible bag, said delivery caused by fluid pressure in said flexible bag, said device having means for increasing said fluid pressure in response to a signal generated when said fluid pressure is less than a desired fluid pressure, said control means comprising: (a) a substantially inflexible base member; (b) a resilient spring plate having a first end and a second end, said plate attached to said base member at said first end, said second end free to flex toward and away from said base member, said second end biased toward said base member; (c) a bladder in flow communication with said flexible bag wherein said bladder inflates in response to an increase in said fluid pressure and deflates in response to a decrease in said fluid pressure, said bladder compressed by said plate between said second end of said plate and said base member such that said second end of said plate flexes away from said base member in response to an inflation of said bladder and flexes toward said base member in response to a deflation of said bladder; and (d) means to generate said signal when said plate flexes toward said base member in response to a deflation of said bladder in response to a decrease in said fluid pressure to less than said desired fluid pressure.

BRIEF DESCRIPTION OF THE DRAWINGS

The invention will now be illustrated with respect to the following drawings illustrating embodiments of the invention in which.

DETAILED DESCRIPTION OF PREFERRED EMBODIMENTS OF THE INVENTION

Figure 1:
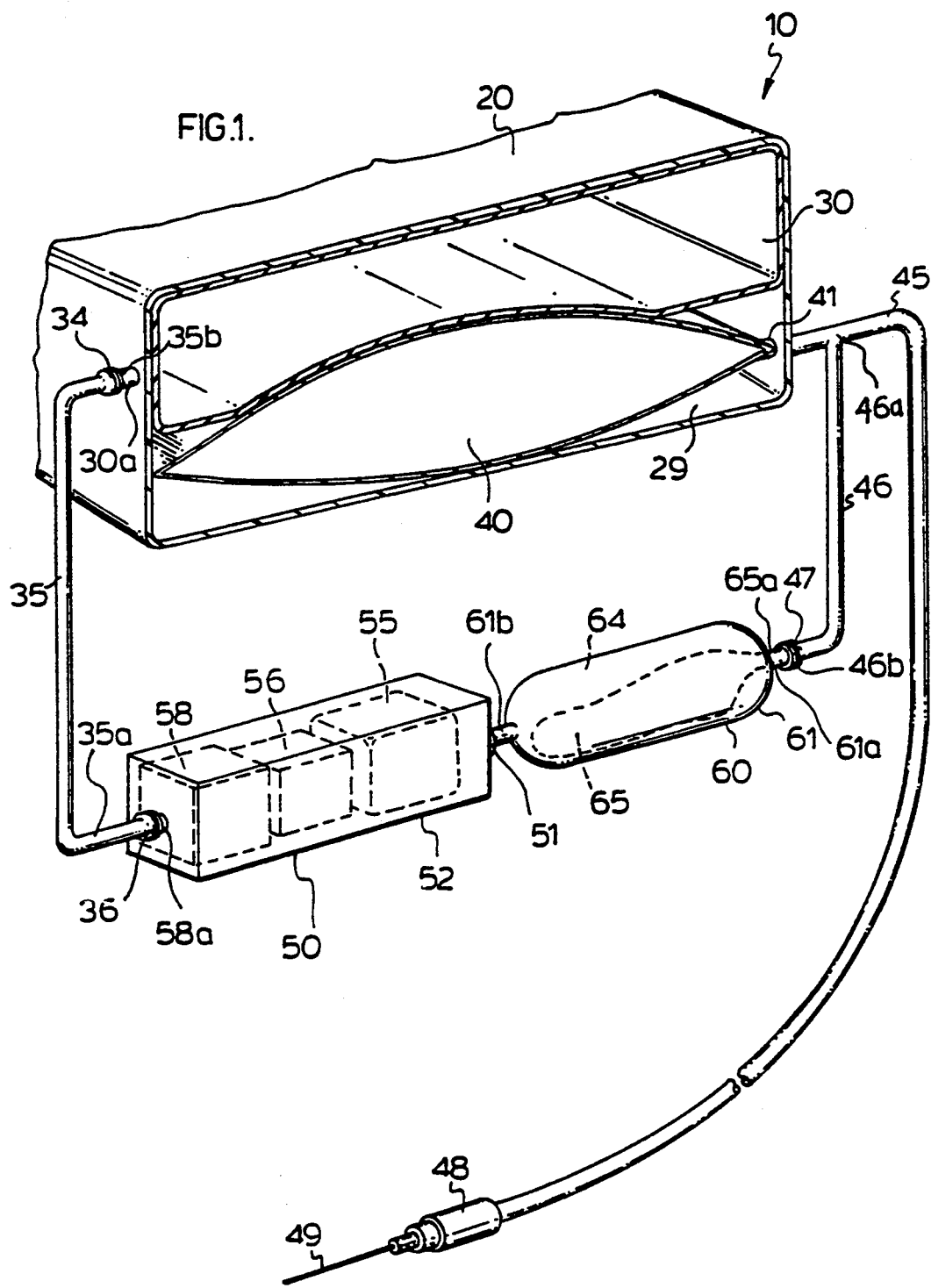
FIG. 1 is a side perspective schematic view of an infusion device illustrated in a preferred embodiment of the invention.
Figure 2:
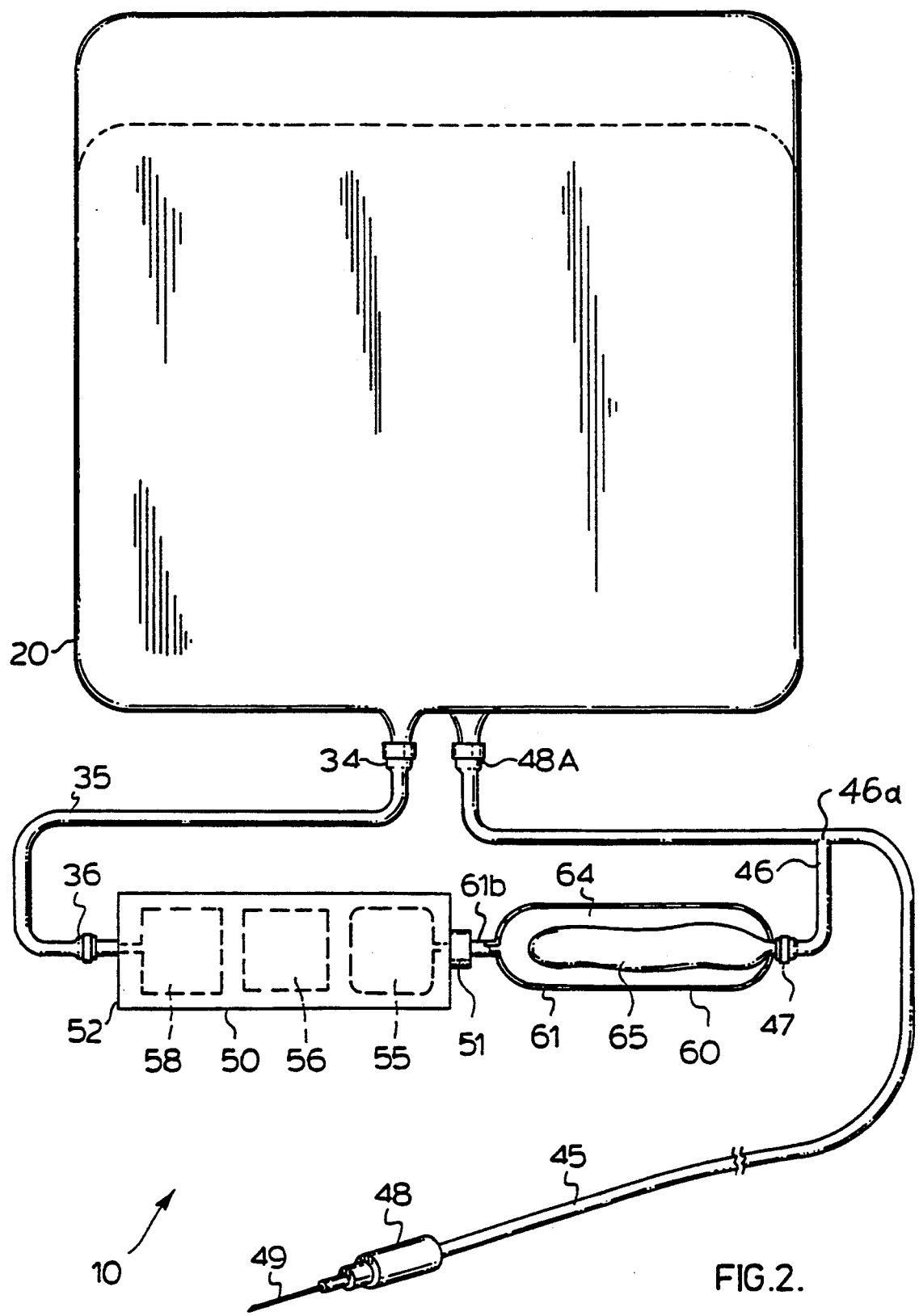
FIG. 2 is a top plan schematic view of the infusion device of FIG. 1 illustrated in a preferred embodiment of the invention.

Referring now to the figures there is illustrated an infusion device 10 used for administering drugs to a patient. Typically the drug is provided in a pre-packaged flexible container 40 which contains up to 500 cm$^2$ of medicament to be administered to the patient. One of the advantages of this invention is that it uses standard sized "drug bags" without the need for having to provide special casettes or the like which is found in the prior art. In using a standard drug bag in conjunction with the present invention the Applicant is no longer required to remain sedentary at a hospital or a clinic while the content of the drug bag is administered to the patient.

The infusion device can therefore be provided in a compact rigid housing 20, which offers resistance to the inflation of an air bag 30 made from flexible materials. Disposed below the air bag 30 is a space 29 which is filled substantially in use by the drug bag 40 which is made from flexible material and contains up to 500 cm$^2$ of the medicament being administered to the patient. The air bag 30 is clamped to a line 35 made of medical grade vinyl and clamped at 34 to a fitting 30(a) provided with the air bag 30. The line 35 is connected with a diaphragm air pump 58 proximate the other end thereof via a clamp 36.

Figure 5:
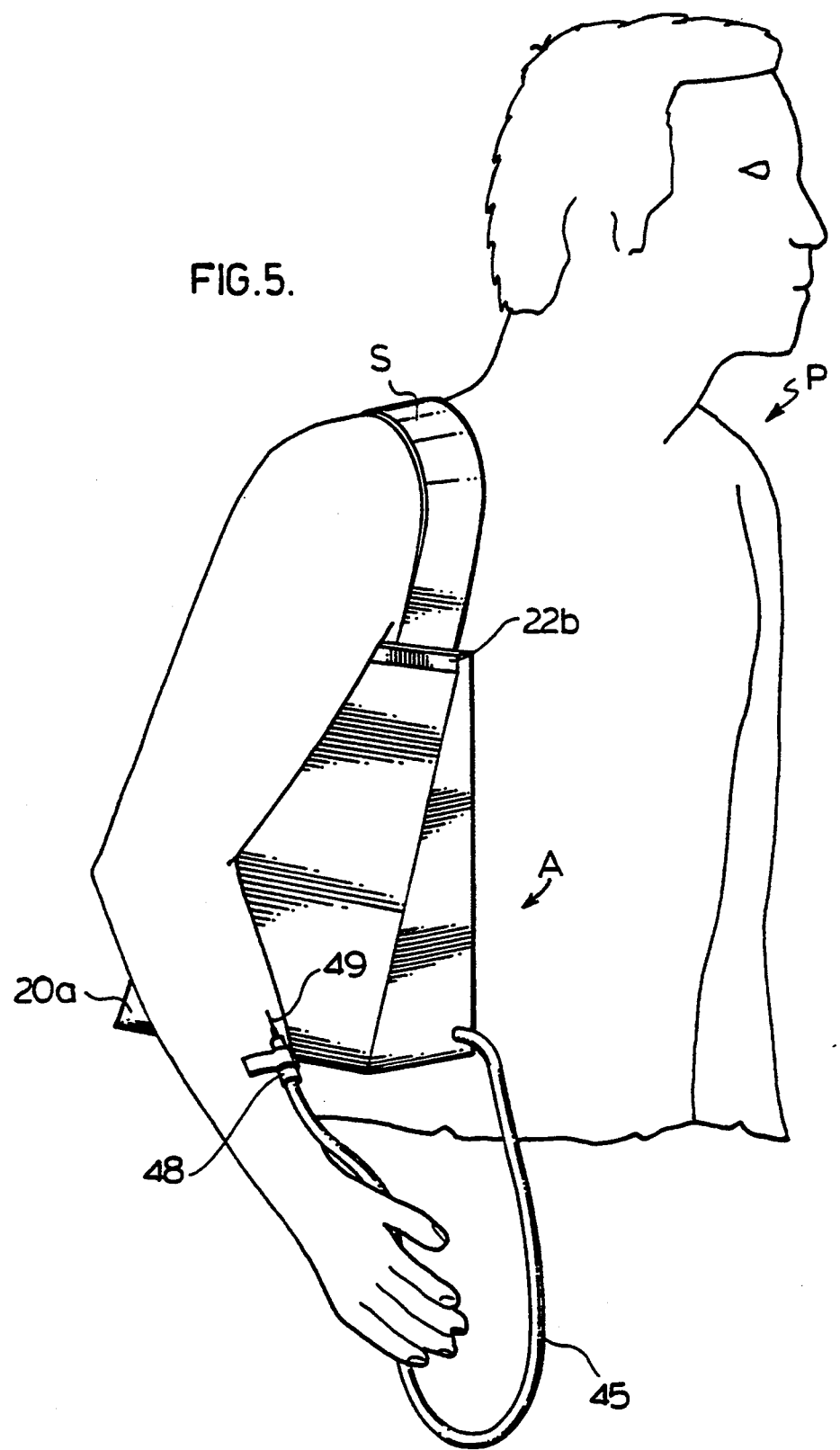
FIG. 5 is a general perspective view of the use of the infusion device of FIG. 4 and illustrated in a preferred embodiment of the invention.

The drug bag 40 is connected at a tapered end thereof 41 by conventional methods such as a clamp to a section of tubing 45 made of medical grade vinyl which extends to the needle 49 and the patient as best seen in FIG. 5. Located adjacent the needle 49 is a precision glass restrictor 48 used to precisely control the amount of drug administered to the patient. A detailed description of these precision restrictors is found in my U.S. Pat. No. 5,059,182 and specifically in relation to the detailed description thereof at for example column 7 line 54 onward, which description is hereby incorporated by reference.

In order for the infusion device 10 to be of use to a patient it is preferred that the housing 20 be separable. No details as to the separation of the housing is provided as it is assumed that those skilled in the art would appreciate the manner in which a housing may be separable into two halls by a hinge, by telescopic relationship of one half being slightly larger than the other half and inter-fitting with that other half, or one portion being slideable in relation to the other portion. The important aspect is that the housing be rigid and include a hollow space 29 so that a drug bag 40 may be placed in the position as shown and affixed to the tubing 45 at clamp 48A. Therefore if more than one type of fluid were being administered to a patient sequentially, for example a saline solution followed by a medicament, then the same apparatus may be used and may be easily set up by the nurse or other medical attendant. The clamps 34 and 48A are known to those skilled in the art and therefore no further description is necessary.

A second line 46 in communication with the first line 45 at juncture 46a is provided to allow for a direct pressure reading to be taken from the line 45 as the medicament is delivered to the patient. At the end 46b of line 46 there is found an impermeable membrane sock 65 contained within an isolation device 60 including a hollow glass receptacle 61 having two ends 61a and 61b. The sock 65 is therefore affixed at the end 61a at end of 65a of the sock with the end of 61a of the glass receptacle. These two portions are therefore clamped to the tube end 46b via clamp 47. Disposed within the isolation device 60 is also an air space 64 which is in communication with the end 61b of the receptacle 61. End 61b is engaged with a control module 50, which includes a transducer 55, by a luer lock fitting. Description of luer lock fittings is found for example in U.S. Pat. No. 4,369,781 assigned to Sherwood Medical Industries Incorporated and describing therein medical luer fittings, the teachings thereof those skilled in the art are referred to for a detailed explanation, such explanation being for a specific luer lock fitting and their parts, function, and use, which description is hereby incorporated by reference. Therefore end 61b of the isolation device 60 is fastened with the control module 50 via luer lock fitting 51 in direct relation with the transducer 55 so that as fluid fills the line 46 and sock 65, the air space 64 will experience a pressure above atmospheric pressure directly proportional to the pressure in the line 45, as the medicament is delivered to the patient. The transducer 55 will therefore have available to it directly the pressure within the section 64. Such reading of pressure will be communicated to the electronic control unit, such as a microprocessor 56, having pre-established set points therewith in relation to the pressure in line 45. Should the pressure therefore in line 45 be below the set point, the microprocessor will communicate with the air pump 58 to pump air from the pump 58 through the line 35 into the air bag 30. The pump 58 is engaged with the air line 35 at end 35a to end 58a of the pump via clamp 36. Also end 35b of the line 35 is engaged with end 30a of the air bag 30 via clamp 34. As the pressure is in,eased in air bag 30 additional pressure will be exerted by the air bag 30 upon drug bag 40, since the housing 20 containing the air bag 30 is a rigid housing having very little resilience whatsoever resulting in any inflation of the bag 30 being entirely (resilience) exerted upon the drug bag 40 over substantially all of its length. The resulting increased pressure from the air bag 30 will provide an increased flow of the medicament contained within the drug bag 40 through to the line 45 on to the patient. Further there will be an increased pressure in the line 45.

Importantly, the infusion device 10 is designed to provide a steady flow of medicament to the patient over the period of time during which the contents of the drug bag are to be delivered. For example, if a drug bag containing 500 cm$^2$ of liquid is provided and it is desired to deliver this medicament to the patient at the rate of 20 milliliters per hour, (although it is expected for the apparatus the range of 10 milliliters to 100 milliliters per hour to be the expected range of operation), it is also desirable to maintain the delivery of the 20 milliliters per hour uniformly over the 60 minutes represented by the hour. It would not be advantageous to the patient to deliver an extreme amount initially and tapering off to a relatively small amount near the end of the administration cycle. In order therefore to achieve this steady state it is important that the pressure be monitored continually within line 45, and yet the device monitoring the pressure transducer 55, be isolated from contaminating the medicament delivered to the patient, and yet provide readings to the microprocessor to control the flow to the patient within the desired range of deviation. It is therefore desirable for the pressure reading at transducer 55 to be communicated to the microprocessor 56 which in turn compares the pressure reading to set points and based on the difference between the set point and the reading and whether the difference is positive or negative, will therefore allow the pump 58 to start or prevent it from starting until such time as the difference is negative for example. In this manner therefore a very precise control of the infusion rate can be obtained.

Figure 3:
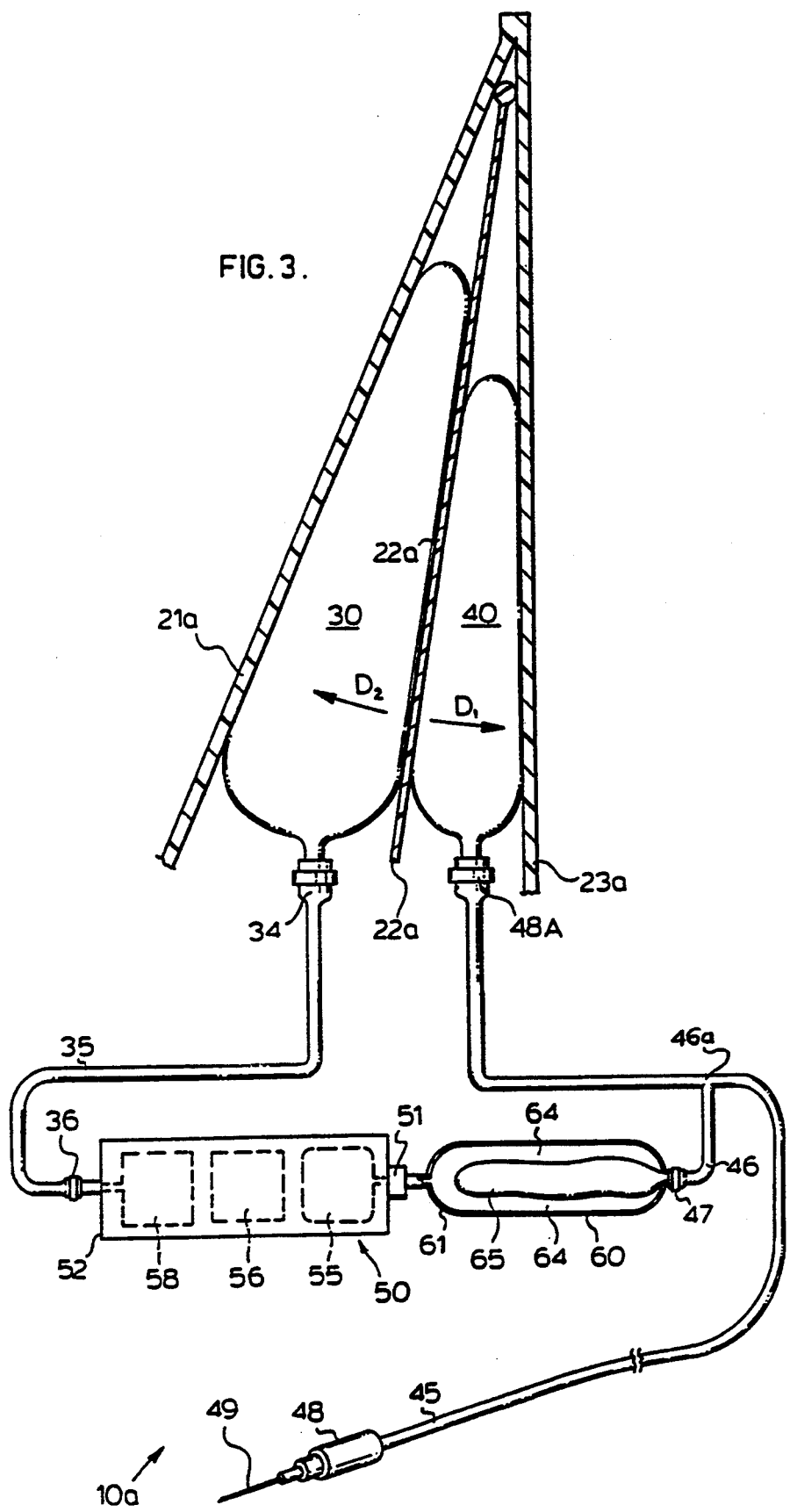
FIG. 3 is a schematic view of the another embodiment of an infusion device illustrated in a preferred embodiment of the invention.
Figure 4:
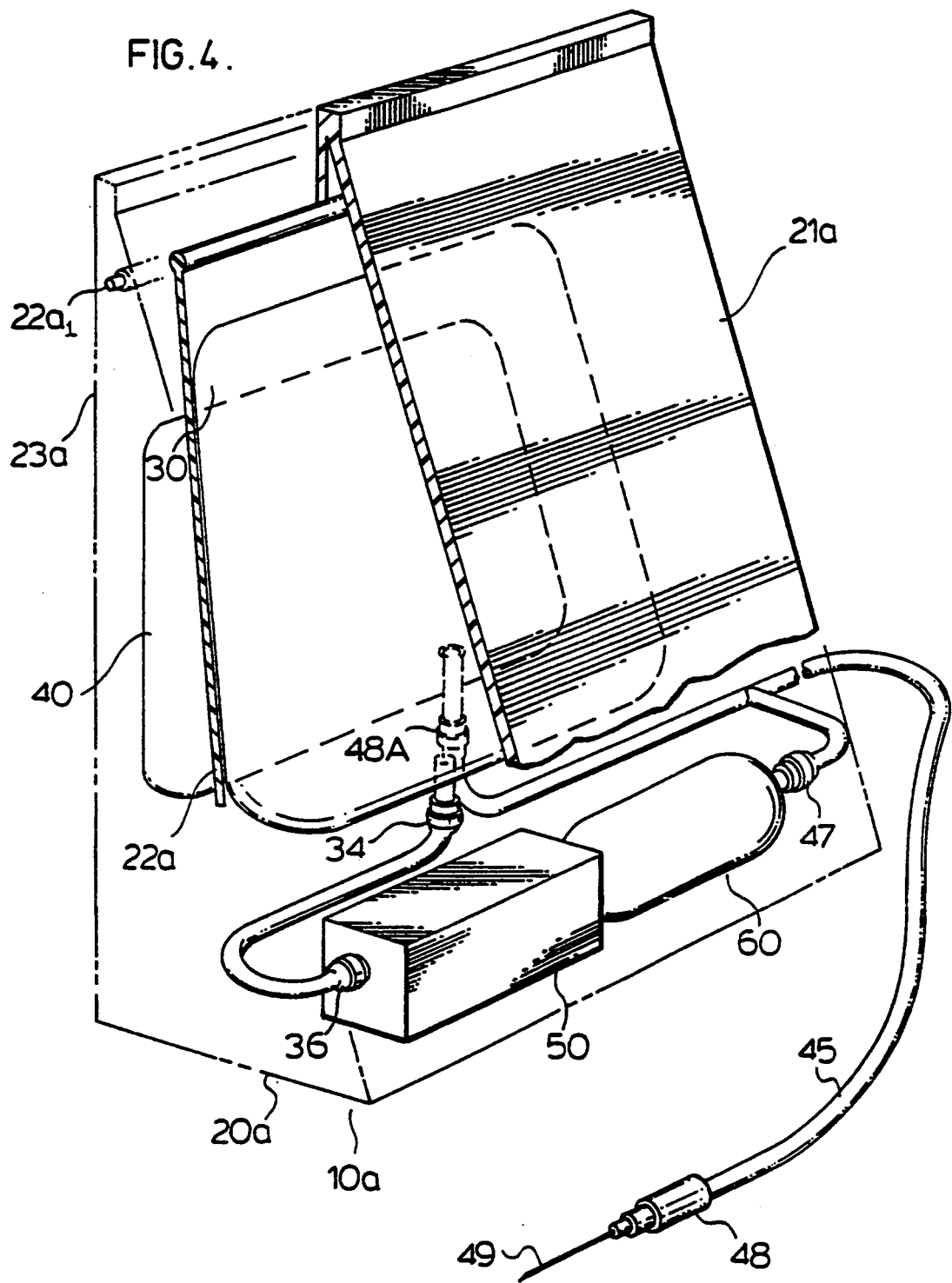
FIG. 4 is a partially cutaway perspective view of the mechanism described in relation to FIG. 3 illustrated in a preferred embodiment of the invention.

Referring to FIGS. 3 to 5 there is described the identical operation of the infusion device 10a with the exception that the housing 20a of the infusion device is shaped substantially as shown in FIG. 5 having a top 21a a bottom 23a and hinged member 22a resting between the air bag 30 and the drug bag 40. The purpose of the plate 22a contained within the housing 20a is to provided a more uniform a pressure over the length of the drug bag 40 as the medicament is delivered to the patient. The plate 22a as best seen in FIG. 4 is pivotally attached via pins 22a1 to the side of housing 20a allowing motion thereof in the directions D1 and D2 as best seen in FIG. 3. The balance of this operation of the infusion device 10a is consistent with that as previously described, with the exception that in relation to FIG. 5 the infusion device is provide with a convenience strap as in those manners which those skilled in the art would know. For example an opening may be provided at flange 22b of the housing for the strap to pass there through at both sides of the housing to form a shoulder bag type apparatus A which may be carried by person "P" in an ambulatory fashion thus freeing person "P"

from having to be left in a sedentary position at a hospital, taking up a hospital bed and the time of the medical professionals; wherein the medication could equally be administered with the patient "P" going about his or her business at a moderate level of activity around the home for example.

Figure 6:
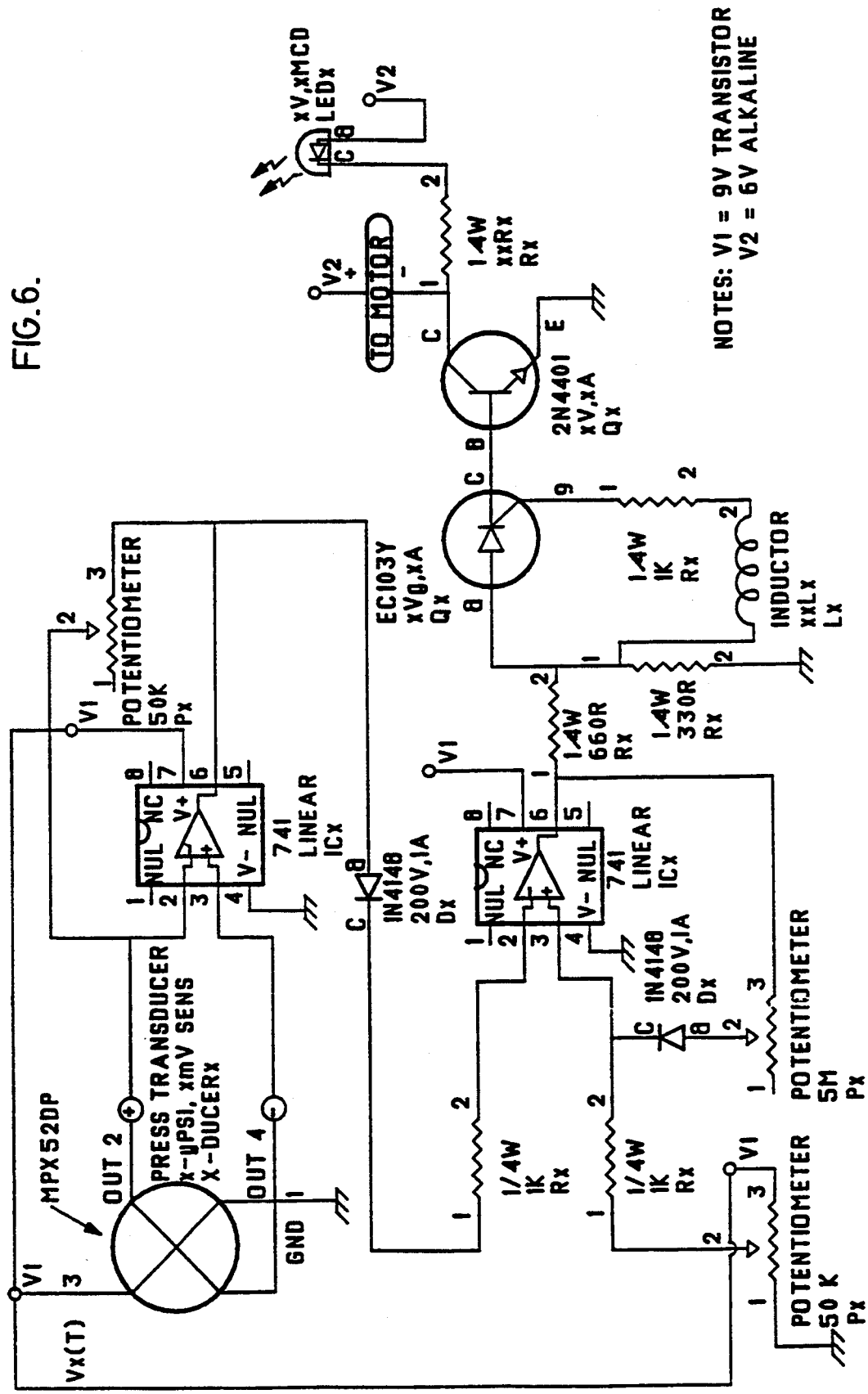
FIG. 6 is a circuit diagram for the operation of a control unit of the infusion device and illustrated in a preferred embodiment of the invention.

FIG. 6 describes one embodiment of many control units that would work with the instant invention. The following description therefore is for the one specific circuit design to accomplish the necessary tasks for operation of the infusion device. However any electronic circuit or device, or any combination of electronic and pneumatic devices which fundamentally provides set points for the expected pressure within line 45 and a comparison therewith with the actual pressure being read from the line 45. Should the difference between the set point and the actual pressure be positive then the motor will turn on to drive the blower fan to inflate the bag 30 until there is no difference or negative difference. Should the pressure difference between the set point and the actual pressure be negative than the motor will not turn on allowing the pressure in the line 45 to reduce toward the set point.

To accomplish this task therefore the circuit provided in FIG. 6 as one embodiment only and without limitation provides a transducer model number MPX 52DP which provides two outputs to a linear integrated circuit in chip form which 8 pin chip includes an or gate connected to input pins 2 and 3 and output pin 6 which fires only if output 2 is less than output 4 from the transducer. The input to pin 2 may be reduced in comparison to the value of the output of the transducer by a potentiometer which may be adjusted so as to allow the value of output 2 to be less than the value of output 4. When this is the case the or gate will allow an output on pin 6 which passes through a diode to prevent any reverse current flow which would cause damage to the integrated circuit. Pin 7 is a return pin to the voltage V1 applied to the transducer.

A signal would then carry on through a resister which would then lower the value of the voltage of the circuit passing through to the second linear integrated circuit which is also an 8 pin chip. Input pins 2 and 3 are provided for the or gate and output 6 is provided for the signal once the or gate fires. The or gate of the second integrated circuit will fire only when the signal from the first integrated circuit is less than the signal resulting from the adjustment of the values of the second set of potentiometers, one of the potentiometers including a diode to prevent reverse current flow thereof and damaging of the second integrated circuit. Therefore when the set points of the two potentiometers of the second integrated circuit are set at certain levels in a manner such that the input to pin 2 will be greater than the input to pin 3 until such a time as the pressure reading in line 45 is less than the set value set via the adjustment provided in the circuitry, the or gate will fire and provide a signal on pin 6 which signal will then be reduced through a silicon controlled rectifier in parallel with an inductor coil which may be for example a meter to obtain a read out convenient to the medical staff or the user so that if the meter is not working the silicon controlled rectifier will not fire since no signal will be provide to the gate of the silicon controlled rectifier. The output of the silicon controlled rectifier will then pass through a transistor at the base thereof which will amplify the signal to a sufficient level to turn on the motor and light the LED to indicate that the motor is turned on when the conditions previously described are present. The fan will than pump up the air bag 30 until such time as the pressure reading in line 45 is above the set point as established by the adjustments in the circuitry and then the silicon controlled rectifier will not fire until such time as the pressure level passes below the set point again.

The above circuit description is provided as an example only and no way limits the variations of circuitry or devices which would work based on advances in technology with the infusion device. It is sufficient that some electronic control unit or combination mechanical, pneumatic and/or electronic be provided which provides the features described above and the comparison of the set point with the actual pressure readings.

Figure 7:
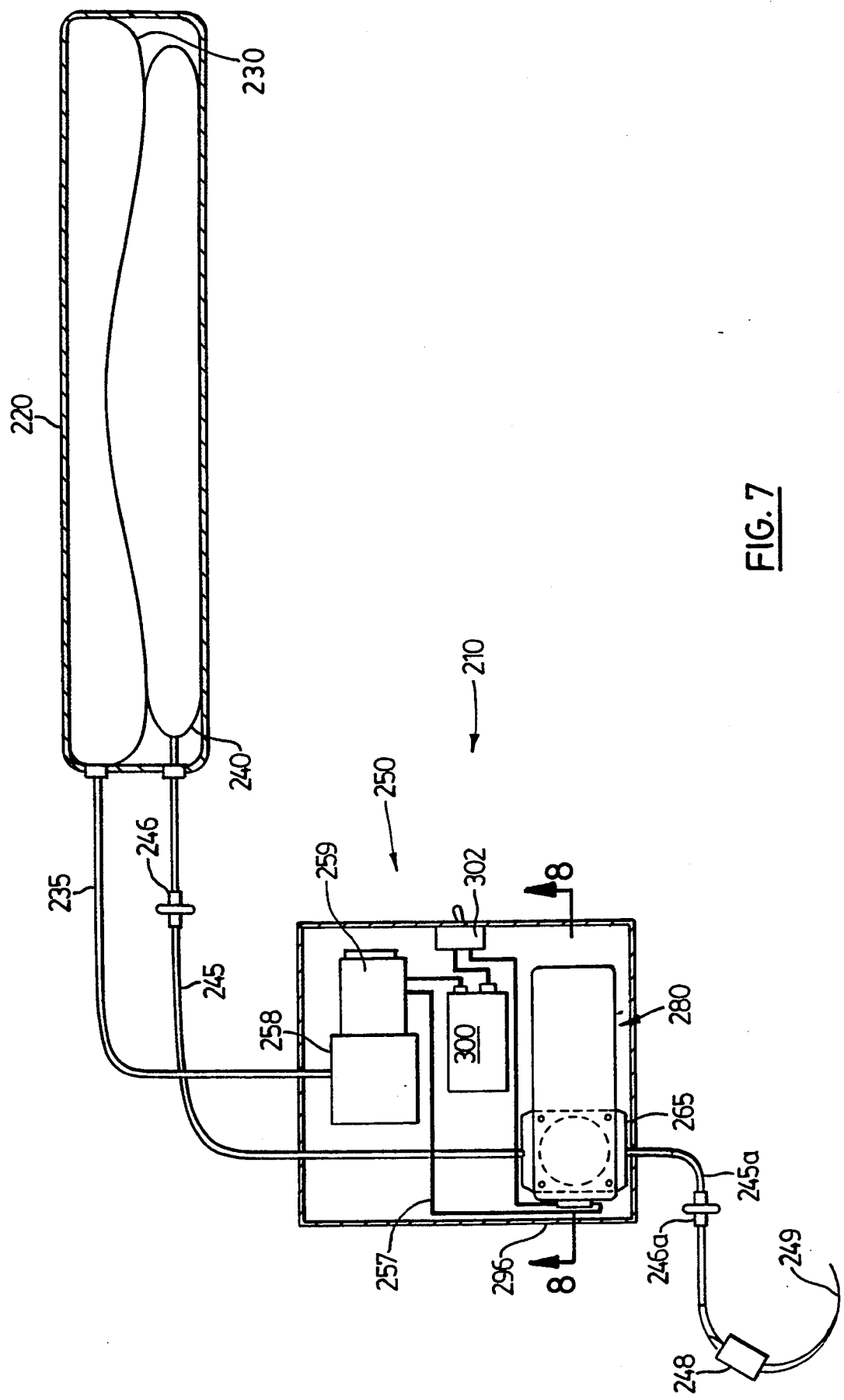
FIG. 7 is a schematic view of another embodiment of an infusion device illustrated in a preferred embodiment of the invention.
Figure 8:
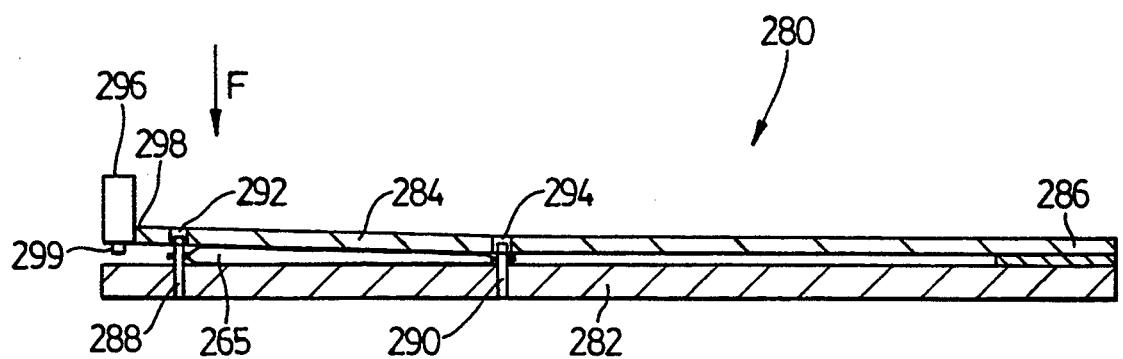
FIG. 8 is a side elevational view of the control unit of the embodiment illustrated in FIG. 7 as viewed along the lines 8—8.

Referring now to FIGS. 7 and 8, there is illustrated another embodiment of the infusion device 210 constructed in accordance with the present invention. A drug bag 240 is filled with a fluid medicament to be delivered to a patient. Drug bag 240 is contained within rigid housing 220 along with flexible air bag 230. As described above, it is preferable that housing 220 be separable to allow access to the interior thereof to permit replacement of drug bag 240 when depleted.

Drug bag 240 is connected to tubing 245 by conventional means. Tubing 245 extends through housing 220. Tubing 245 is in flow communication with the contents of drug bag 240.

Air bag 230 is connected to air line 235. Air line 235 also extends through rigid housing 220. Air line 235 is in turn pneumatically connected to air pump 258. Preferably, air pump 258 is a pneumatic or diaphragm air pump. Air pump 258 is driven by electric motor 259 to inflate air bag 230 when electric motor 259 is activated. Electric motor 259 is activated when the electric circuit 257 is closed. This will be further described below.

Tubing 245 is connected to diaphragm or bladder 265 which is also connected with a further length of tubing 245a which is at its end connected to needle 249 through which the fluid medicament of drug bag 240 is administered to a patient. Connected in series with the further length of tubing 245a, is flow restrictor 248. Tubing 245 or further tubing 245a may include one-way valves 246 and 246a to prevent any back flow of fluids into drug bag 240.

Bladder 265 and tubing 245/245a are composed of a medical grade resilient flexible material such as medical grade rubber or vinyl. Bladder 265 is inflatable and deflatable in proportion to the fluid pressure within tubing 245/245a (which is proportionate to the fluid pressure within drug bag 240).

When inflated, air bag 230, contained within rigid housing 220 with drug bag 240, applies a direct pressure to drug bag 240 increasing the fluid pressure therein, thereby motivating the fluid within drug bag 240 to flow through tube 245 toward infusion needle 249. An increased pressure within drug bag 240 results in an increased pressure within tubing 245/245a. As a result of an increased pressure within tubing 245/245a, bladder 265 will inflate.

With reference to FIG. 8, the pressure sensor assembly 280 of control module 250 may be described in greater detail. Pressure sensor 280 comprises bladder 265 in flow communication with tubes 245 and 245a (as previously described with reference to FIG. 7). Bladder 265 is sandwiched between a substantially rigid base 282 and a flexible plate 284 which is attached at one end 286 to base 282. Plate 284 is flexible, resilient and spring-like and is biased toward base 282 in the direction of arrow F to compress bladder 265.

Guide pins 288 and 290 included in base member 282 correspond to guide holes 292 and 294 through plate member 284. Guide pins 288 and 290 and guide holes 292 and 294 guide the movement of plate 284 toward and from base member 282.

When inflated as result of increased pressure in tubing 245/245a, bladder 265 will flex plate 284 against its bias in the direction away from base 282. Conversely, when the fluid pressure in tubing 245/245a decreases, bladder 265 will be compressed by plate 284 as it flexes in the direction of its bias toward base 282.

Switch circuit 296 is attached to end 298 of plate 284. Switch circuit 296 is preferably a microswitch which requires little force to trigger actuator 299 when it is pressed against base 282. Switch 296 is electrically connected in series to electrical circuit 257 between power supply 300 and electric motor 259 (best depicted in FIG. 7). Switch 296 is normally open, meaning that electrical circuit 257 is not closed until actuator 299 is triggered. With reference to both FIGS. 7 and 8, when the circuit between microswitch 296, electric motor 259, power supply 300 and on/off switch 302 is closed, electric motor 259 will be activated and pump 258 will pump air into air bag 230, thereby increasing the space occupied by air bag 230 within rigid housing 220 and will increase the fluid pressure within drug bag 240.

Since switch 296 is normally open, when actuator 299 is in the position shown in FIG. 8, electrical circuit 257 interrupted (or open) and therefore air pump 258 does not pump air into air bag 230. Therefore, as fluid drains from drug bag 240, the fluid pressure within drug bag 240 is decreased. The decrease in fluid pressure within drug bag 240 (and tubes 245/245a) will cause a deflation of bladder 265 compressed by plate 284. At a point where the fluid pressure within drug bag 240 is less than a certain desired value, actuator 299 of switch 296 will be depressed against base 282, as a result of the movement of plate 284 in the direction of its bias as shown by arrow F, and will close circuit 257 thus causing air pump 258 to inflate air bag 230 and increase the pressure in drug bag 240. The inflation of air bag 230 will continue until circuit 257 is again opened by the flexing of plate 284 (and, therefore, switch 296) from base 282. The inflation of bladder 265 caused by the inflation of air bag 220 and the resulting increased fluid pressure in drug bag 230 will cause the flexing of metal plate 284 away from base 282 to cause actuator 299 to be again suspended above base 282, again opening circuit 257. This cycle repeats itself until the drug bag is depleted, at which time on/off switch 302 may be used to open circuit 257. This feedback control loop permits accurate maintenance of a desired fluid pressure in the tubing leading from the drug bag.

Other configurations of switches, etc. may be used in cooperation with plate 284 to cause the activation of air pump 258. For example, a normally closed switch in series with circuit 257 may be interposed between plate 284 and another base member (not shown) above plate 284. Therefore, the circuit will be opened when bladder 265 is inflated in response to a fluid pressure at or above a desired fluid pressure. The device may also include a reversible pump or other means to release pressure from or deflate the inflatable bag if necessary.

Referring to FIG. 8, it will be understood that the desired fluid pressure may be selected by adjusting the extent to which switch 296 extends upwardly or downwardly from plate 284.

An advantage of the invention, particularly as embodied in FIGS. 7 and 8, is that the portable infusion device is very inexpensive to manufacture and therefore may be disposed once used. The advantages of such an inexpensive, therefore disposable infusion device will be apparent to those skilled in the art.

As many changes can be made to the preferred embodiments of the invention without departing from the scope of the invention, it is intended that all material contained herein be interpreted as illustrative of the invention and not in a limiting sense.

The embodiments of the invention in which an exclusive privilege or property is claimed are as follows:

1. A portable infusion device comprising:
   (a) a rigid housing, said housing having an interior space;
   (b) a flexible bag contained within said interior space, said flexible bag filled with a fluid to be delivered, said flexible bag having an outlet;
   (c) a tube having a first end attached to said flexible bag outlet in flow communication with said fluid to be delivered, said tube having a second end to which said fluid is delivered in use;
   (d) an inflatable bag contained within said interior space, said inflatable bag inflatable to press the flexible bag thus creating a fluid pressure within said flexible bag causing a tendency for said fluid to flow from said flexible bag through said tube for delivery to said second end of said tube;
   (e) means for inflating said inflatable bag in response to a signal;
   (f) control means which responds to said fluid pressure within said flexible bag for generating said signal when said fluid pressure in said flexible bag is less than a desired fluid pressure, said control means comprising:
      (i) a substantially inflexible base member;
      (ii) a resilient spring plate having a first end and a second end, said plate attached to said base member at said first end, said second end free to flex toward and away from said base member, said second end biased toward said base member;
      (iii) a bladder in flow communication with said flexible bag wherein said bladder inflates in response to an increase in said fluid pressure and deflates in response to a decrease in said fluid pressure, said bladder compressed by said plate between said second end of said plate and said base member such that said second end of said plate flexes away from said base member in response to an inflation of said bladder and flexes toward said base member in response to a deflation of said bladder; and
      (iv) means to generate said signal when said plate flexes toward said base member in response to a deflation of said bladder in response to a decrease in said fluid pressure to less than said desired fluid pressure.

2. The portable infusion device of claim 1 wherein said inflation means comprises a diaphragm air pump pneumatically coupled with said inflatable bag.

3. The portable drug infusion device of claim 1 wherein:
   (a) said resilient spring plate comprises a thin metal plate;

(b) said inflating means comprises an electric air pump and an air pump power supply, said air pump inflating said inflatable bag in response to an electrical current from said air pump power supply; and (c) said signal generating means comprises a normally open switch circuit electrically connected in series between said electric air pump and said air pump power supply, said switch circuit closed by said second end of said metal plate when flexed toward said base member in response to a deflation of said bladder in response to a decrease in said fluid pressure to less than said desired fluid pressure.

4. The portable drug infusion device of claim 3 wherein said control means further comprises:

(d) a second switch circuit electrically connected in series between said electric air pump and said air pump power supply, said second switch circuit opened by said second end of said metal plate when flexed away from said base member in response to an inflation of said bladder in response to an increase in said fluid pressure to greater than a maximum desired fluid pressure, said second switch circuit interrupting said electrical current to said air pump when opened.

5. The portable drug infusion device of claim 3 wherein said bladder, said flexible bag and said tube are composed of a medical grade vinyl.

6. In a portable infusion device, means for controlling delivery of a fluid from a flexible bag, said delivery caused by fluid pressure in said flexible bag, said device having means for increasing said fluid pressure in response to a signal generated when said fluid pressure is less than a desired fluid pressure, said control means comprising:

(a) a substantially inflexible base member;

(b) a resilient spring plate having a first end and a second end, said plate attached to said base member at said first end, said second end free to flex toward and away from said base member, said second end biased toward said base member;

(c) a bladder in flow communication with said flexible bag wherein said bladder inflates in response to an increase in said fluid pressure and deflates in response to a decrease in said fluid pressure, said bladder compressed by said plate between said second end of said plate and said base member such that said second end of said plate flexes away from said base member in response to an inflation of said bladder and flexes toward said base member in response to a deflation of said bladder; and (d) means to generate said signal when said plate flexes toward said base member in response to a deflation of said bladder in response to a decrease in said fluid pressure to less than said desired fluid pressure.

7. The portable drug infusion device of claim 6 wherein:

(a) said resilient spring plate comprises a thin metal plate;

(b) said fluid pressure increasing means comprises an inflatable bag inflated by inflating means, said inflatable bag adapted to press against said flexible bag to increase said fluid pressure in said flexible bag;

(c) said inflating means comprises an electric air pump and an air pump power supply, said air pump inflating said inflatable bag in response to an electrical current from said air pump power supply; and (d) said signal generating means comprises a normally open switch circuit electrically connected in series between said electric air pump and said air pump power supply, said switch circuit closed by said second end of said metal plate when flexed toward said base member in response to a deflation of said bladder in response to a decrease in said fluid pressure to less than said desired fluid pressure.

8. The portable drug infusion device of claim 7 wherein said control means further comprises:

(e) a second switch circuit electrically connected in series between said electric air pump and said air pump power supply, said second switch circuit opened by said second end of said metal plate when flexed away from said base member in response to an inflation of said bladder in response to an increase in said fluid pressure to greater than a maximum desired fluid pressure, said second switch circuit interrupting said electrical current to said air pump when opened.

9. The portable drug infusion device of claim 7 wherein said bladder, said flexible bag and said tube are composed of a medical grade vinyl.

* * * * *